United States Patent
Hsieh et al.

(10) Patent No.: US 8,969,827 B2
(45) Date of Patent: Mar. 3, 2015

(54) SPECIMEN PREPARATION FOR TRANSMISSION ELECTRON MICROSCOPY

(75) Inventors: Yong-Fen Hsieh, Hsinchu (TW);
Chih-Hsun Chu, Hsinchu (TW);
Pradeep Sharma, Hsinchu (TW);
Yu-Feng Ko, Hsinchu (TW); Chung-Shi Yang, Miaoli County (TW); Lin-Ai Tai, Miaoli County (TW); Yu-Ching Chen, Miaoli County (TW)

(73) Assignees: Materials Analysis Technology (US) Corp., San Jose, CA (US); National Health Research Institutes, Miaoli County (TW)

( * ) Notice: Subject to any disclaimer, the term of this patent is extended or adjusted under 35 U.S.C. 154(b) by 290 days.

(21) Appl. No.: 13/544,019

(22) Filed: Jul. 9, 2012

(65) Prior Publication Data

US 2014/0007709 A1    Jan. 9, 2014

(51) Int. Cl.
| | | |
|---|---|---|
| *B82Y 35/00* | (2011.01) | |
| *G01N 1/40* | (2006.01) | |
| *G01N 23/02* | (2006.01) | |
| *G01N 33/49* | (2006.01) | |

(52) U.S. Cl.
USPC ....... 250/440.11; 250/304; 250/307; 977/881

(58) Field of Classification Search
CPC ... B01L 3/508; B01L 3/50857; B01L 3/5088; B01L 2200/0678; B01L 2300/0822; B81B 1/00; B81B 1/004; B82Y 35/00; G01N 1/4022; G01N 23/02; G01N 2001/4027; G01N 2223/102; G01N 2223/307
USPC .................. 73/863.12; 250/304, 307, 440.11; 977/881
See application file for complete search history.

(56) References Cited

U.S. PATENT DOCUMENTS 3,432,275 A * 3/1969 Unger ................... B01L 3/5088
7,573,031 B2 * 8/2009 Behar et al. ............. B01L 3/508
(Continued)

FOREIGN PATENT DOCUMENTS

CN    102527117 A  *  7/2012   ............... B01L 3/00
CN    102539503 A  *  7/2012   ........... G01N 27/403
(Continued)

OTHER PUBLICATIONS

Robert NandKumar Karnik, Manipulation and Sensing of Ions and Molecules in Nanofluidic Devices, Fall 2006, Ph.D thesis in Engineering-Mechanical Engineering at University of California at Berkeley, (199 total pages, UMI microform 3253920, copyright 2007 by ProQuest Information and Learning Company).*

(Continued)

*Primary Examiner* — Thomas P Noland
(74) *Attorney, Agent, or Firm* — Hsiu-Ming Saunders; Intellectual Property Connections, Inc.

(57) ABSTRACT

A specimen kit having a tiny chamber is disclosed for a specimen preparation for TEM. The space height of the chamber is far smaller than dimensions of blood cells and therefore is adapted to sort nanoparticles from the blood cells. The specimen prepared under this invention is suitable for TEM observation over a true distribution status of nanoparticles in blood. The extremely tiny space height in Z direction eliminates the possibility of aggregation of the nanoparticles and/or agglomeration in Z direction during drying; therefore, a specimen prepared under this invention is suitable for TEM observation over the dispersion and/or agglomeration of nanoparticles in a blood.

8 Claims, 9 Drawing Sheets

(56) References Cited

U.S. PATENT DOCUMENTS

| | | | |
|---|---|---|---|
| 7,807,979 B2 | 10/2010 | Liu et al. | |
| 8,475,739 B2 * | 7/2013 | Holmes et al. | 422/509 |
| 2004/0197843 A1 * | 10/2004 | Chou et al. | 435/7.92 |
| 2010/0193398 A1 * | 8/2010 | Marsh et al. | 206/710 |
| 2013/0264476 A1 * | 10/2013 | Damiano et al. | 250/440.11 X |
| 2014/0042318 A1 * | 2/2014 | Yaguchi et al. | 250/440.11 X |

FOREIGN PATENT DOCUMENTS

| | | | |
|---|---|---|---|
| WO | WO 2012018827 A2 * | 9/2012 | H01J 37/20 |
| WO | WO 2012147632 A1 * | 11/2012 | H01J 37/20 |
| WO | WO 2014011563 A1 * | 1/2014 | B01L 3/508 |

OTHER PUBLICATIONS

Daniel Sanchez et al., Noncontact Measurement of the Local Mechanical Properties of Living Cells Using Pressure Applied Via a Pipette, Biophysical Journal, 95(6), pp. 3017-3027, Sep. 15, 2008, published online May 30, 2008, doi:10.1529/biophysj.108.129551, downloaded from http://www.ncbi.nlm.nih.gov/pmc/articles/PMC2527257/ on Jul. 31, 2014.*

Lin-Ai Tai et al, "Quantitaitve characterization of nanoparticles in blood by transmission electron microscopy with a window-type microchip nanopipet", Analytical Chemistry, vol. 84, pp. 6312-6316 (2012), pub. Jul. 16, 2012.

* cited by examiner

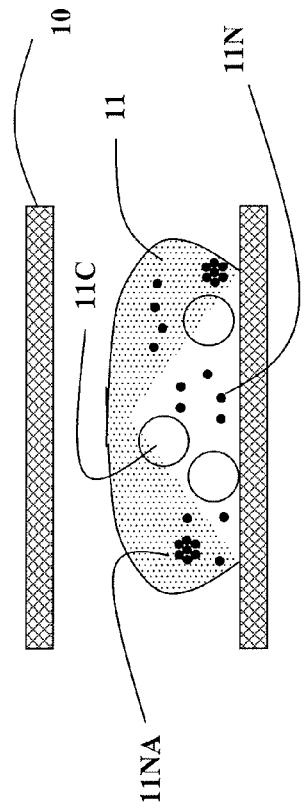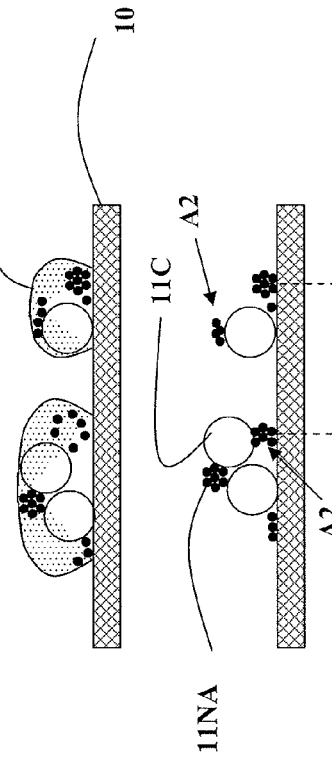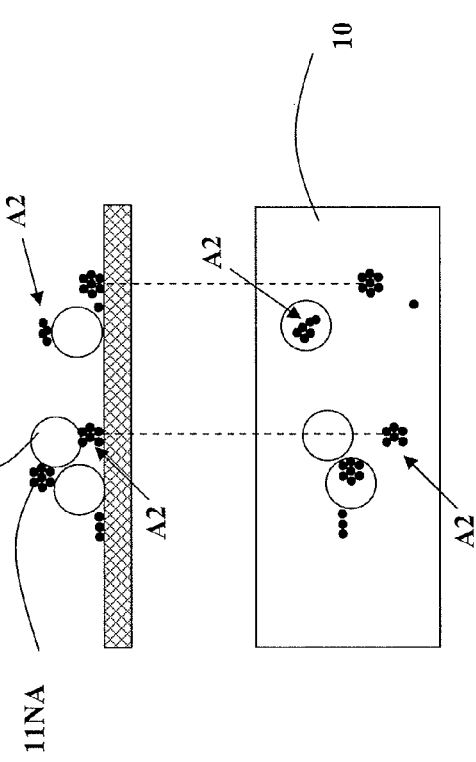
Fig. 2A
Prior Art
Fig. 2B
Prior Art
Fig. 2C
Prior Art
Fig. 2D
Prior Art
Fig. 2E
Prior Art

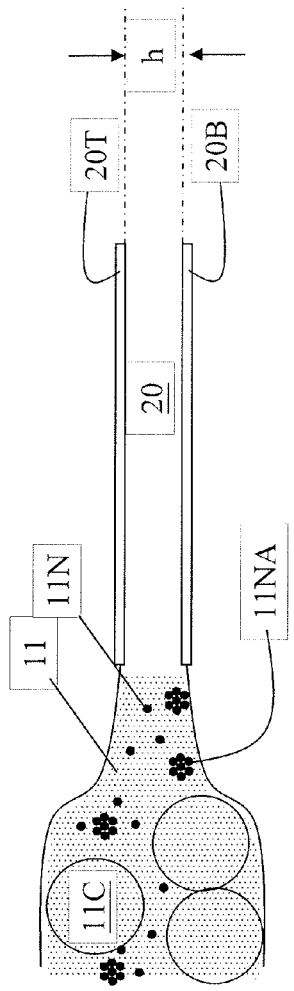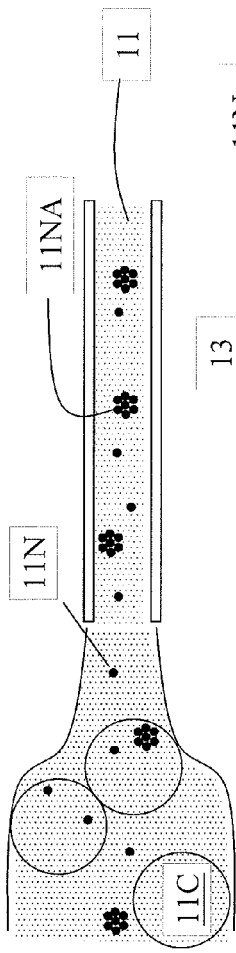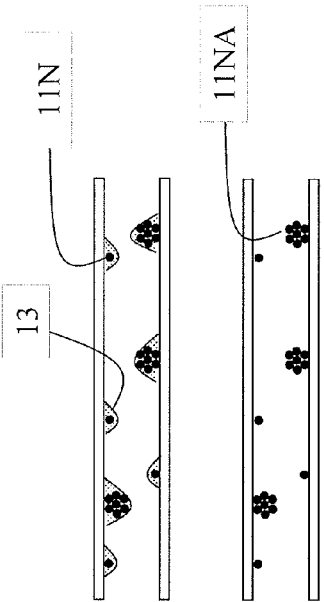
Fig. 4A
Fig. 4B
Fig. 4C
Fig. 4D
Fig. 4E

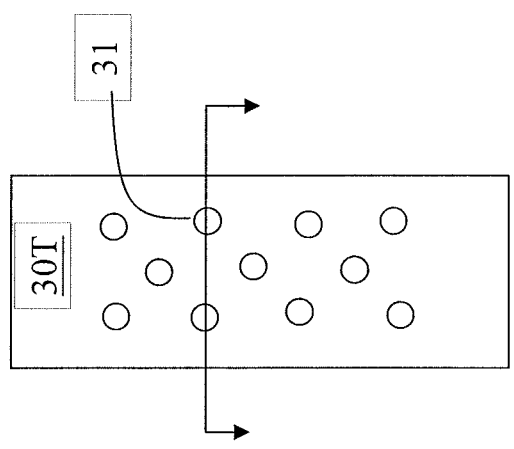
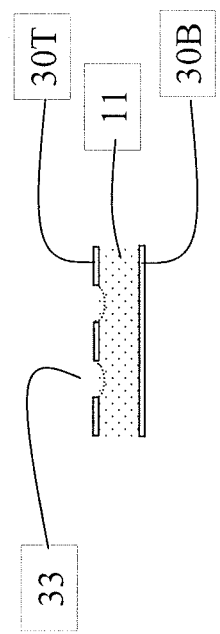
Fig. 8A
Fig. 8B

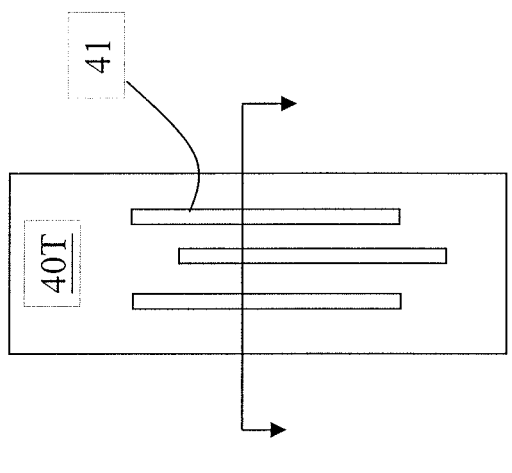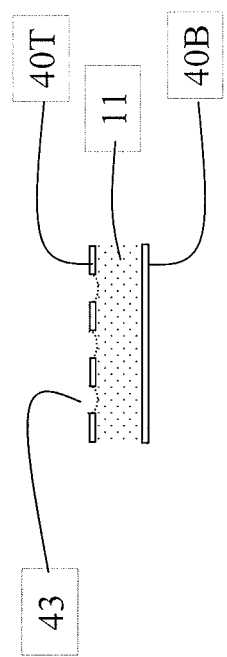
Fig. 9A
Fig. 9B

SPECIMEN PREPARATION FOR TRANSMISSION ELECTRON MICROSCOPY

BACKGROUND

1. Technical Field

The present invention relates to preparation of a specimen suitable for observation under a transmission electron microscope (TEM), which reflects the true distribution status of nanoparticles in a blood sample, either in dispersion or agglomeration.

2. Description of Related Art

FIG. 1A-E show a first specimen prepared according to a traditional method.

FIG. 1A shows a traditional substrate 10, which is usually a piece of copper.

FIG. 1B shows a drop of blood sample 11 placed on the top surface of the substrate 10. The blood sample 11 contains, among others, nanoparticles 11N, and blood cells 11C. The average diameter of a red blood cell (RBC) is 6 to 8 micrometers. The average diameter of a white blood cell (WBC) is 10 to 12 micrometers. A blood cell 11C has a dimension in μm, which is larger than the dimension of a nanoparticle.

FIG. 1C shows a drop of blood sample 11 evaporates during drying. The drop of blood sample shrinks and a plurality of smaller droplets are formed. The surface tension 13 of each droplet drags the components therein closer and closer. The components undergo gatherings.

FIG. 1D illustrates two groups of aggregates A1 of nanoparticles 11N are formed. The concentrating effect of the components within each droplet is caused by a surface tension 13 during drying, causing formation of aggregates A1 of nanoparticles. The aggregates A1 of nanoparticles in the prepared sample had appearances similar to nanoparticle-agglomerates, which may cause a confusion between aggregates and agglomerates and give wrong information to an observer when observing under TEM.

FIG. 1E shows a top view of FIG. 1D. Two groups of aggregates A1 of nanoparticles 11N are formed. The specimen of FIG. 1E does not reflect the true status of nanoparticles 11N, which is evenly dispersed in the blood sample 11 as evidenced by FIG. 1B.

Now, paying attention to nanoparticles 11N only. One of the purposes to examine a specimen of blood sample is to observe the status of nanoparticles 11N in the original blood sample, either in dispersion or agglomeration. However, a specimen prepared by a traditional method does not reflect the original or true status of nanoparticles 11N in the original blood sample, either in dispersion or agglomeration. As shown in FIGS. 1D-E, which shows aggregates A1 of nanoparticles 11N, false information has been displayed under TEM due to a surface tension 13 between the droplets during drying. It is desired that the true status of nanoparticles 11N in the original blood sample can be reflected, either in dispersion or agglomeration.

FIGS. 2A-E show a second specimen prepared according to a traditional method.

FIG. 2A shows a traditional substrate 10, a copper grid.

FIG. 2B shows a drop of blood sample 11 placed on the top surface of the substrate 10. The blood sample 11 contains, among others, dispersed nanoparticles 11N, nanoparticle-agglomerates 11NA, and blood cells 11C.

FIG. 2C shows the liquid evaporates during drying, the drop of blood sample shrinks and smaller droplets are formed. The surface tension 13 of each droplet drags the components closer and closer.

FIG. 2D shows aggregates A2 of nanoparticles are formed.

FIG. 2E shows the top view of FIG. 2D. Two groups of aggregates A2 of nanoparticles 11N are formed. Actually, the aggregates A2 do not exist in the original blood sample, see FIG. 2B. The specimen of FIG. 2E gives false information to an observer.

Now, paying attention to nanoparticle-agglomerates 11NA only. One of the purposes to examine a specimen of a blood sample under TEM is to observe whether any nanoparticle-agglomerate exists in an original blood sample. However, a specimen prepared by a traditional method does not reflect the true number of nanoparticle-agglomerates 11NA. Several aggregates A2 of nanoparticles 11N, counterfeits of nanoparticle-agglomerates 11NA, are present in FIGS. 2D-E. The aggregates A2 are caused by the surface tension 13 of the droplets during drying. It is desired that the true situation of nanoparticles in the specimen can be observed, either in dispersion or agglomeration.

BRIEF DESCRIPTION OF THE DRAWINGS

FIGS. 2A-E show the second specimen prepared according to a traditional method.

FIGS. 4A-E show the second specimen prepared according to the present invention.

FIGS. 8A-B illustrate the top substrate 30T and the chamber of the second specimen kit, respectively.

FIGS. 9A-B illustrate the top substrate 40T and the chamber of the second specimen kit, respectively.

DETAILED DESCRIPTION OF THE INVENTION

This invention discloses a method of preparing a specimen with a specimen kit which has a tiny chamber. The height of the chamber is configured to be smaller than the diameter of a red blood cell (RBC). A RBC is smaller than a white blood cell (WBC). Thus, all blood cells are screened from entering the chamber of the specimen kit. The absence of blood cells in the specimen reduces interference with observation of nanoparticles, and therefore enhances the quality and quantity check of the specimen. The small chamber of the specimen kit limits a blood sample inside and eliminates the effect of surface tensions during drying. The specimen prepared according to the invention makes it possible to detect the true distribution status of nanoparticles in the original blood sample, either in dispersion and/or agglomeration.

FIGS. 3A-E illustrate the first specimen prepared according to the present invention.

Figure 1A:
FIGS. 1A-E show the first specimen prepared according to a traditional method.
Figure 1B:
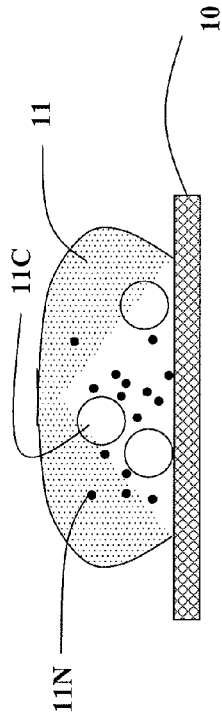
Figure 1C:
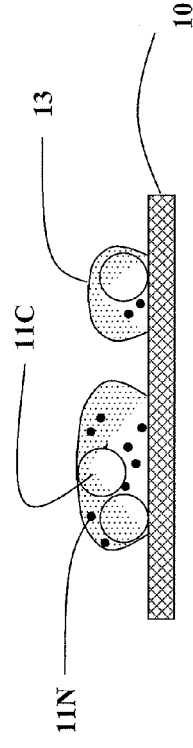
Figure 1D:
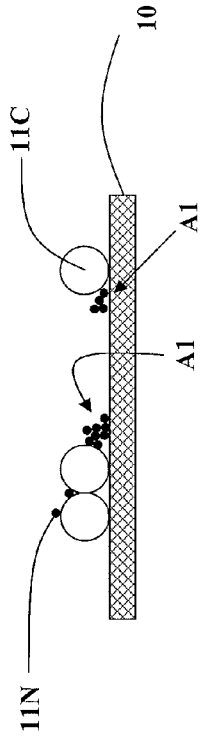
Figure 1E:
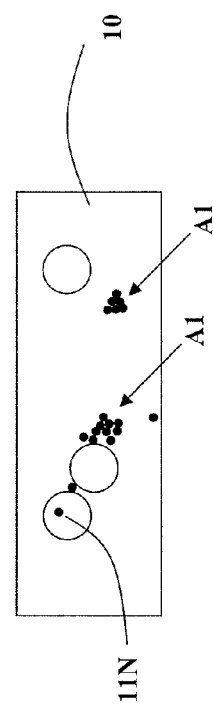
Figure 3A:
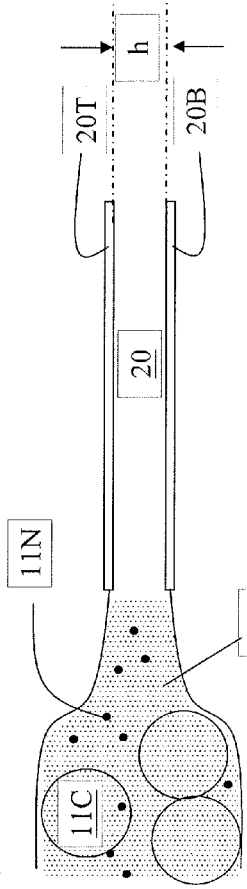
FIGS. 3A-E show the first specimen prepared according to the present invention.

FIG. 3A shows a blood sample 11 is ready to be injected into a chamber 20 of a specimen kit. The blood sample 11 contains nanoparticles 11N and blood cells 11C. A chamber 20 is formed between a top substrate 20T and a bottom substrate 20B. The height h between the top substrate 20T and the bottom substrate 20B is less than the diameter of a red blood cell (RBC). Thus, all RBCs and white blood cells (WBCs) are screened from entering the chamber 20. A height of 10 μm for the chamber 20 is enough for TEM observation of the distribution status of nanoparticles in the blood sample, either in dispersion or agglomeration.

Figure 3B:
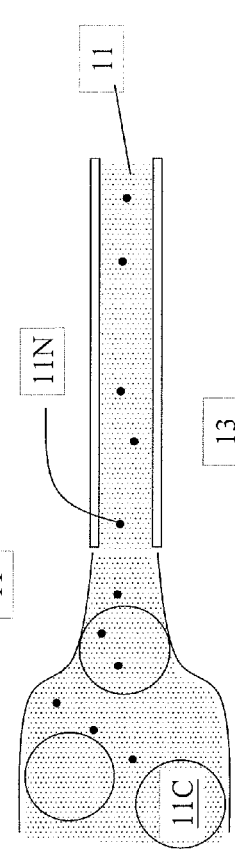

FIG. 3B shows nanoparticles 11N in a blood sample 11 entering the chamber 20. Blood cells 11C do not enter the chamber 20 due to their larger dimensions.

Figure 3C:
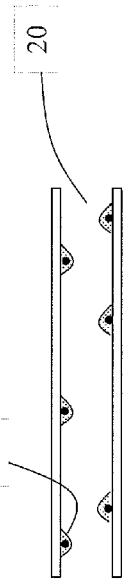

FIG. 3C shows a drying process is performed to the blood sample 11 of FIG. 3B. The blood sample 11 within the chamber 20 is dried and a plurality of small droplets are formed. Each droplet wraps a single nanoparticle 11N and attaches onto the inner surface of the chamber 20 due to the adhesion force 13 of the droplet.

Figures 3D, 3E:
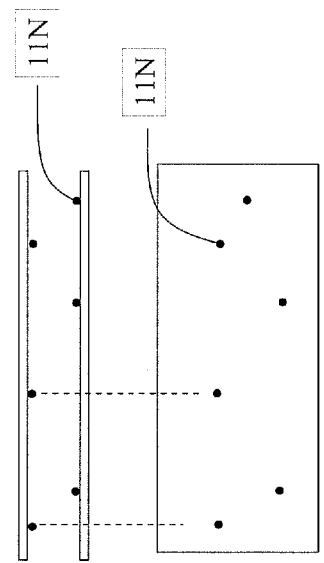

FIG. 3D shows some nanoparticles 11N attached to the bottom surface of the top substrate 20T after drying, and some nanoparticles 11N attached to the top surface of the bottom substrate 20B after drying. The tiny height h between the two substrates 20T, 20B limits the number of the nanoparticles 11N distributed in Z direction and hence, eliminates the possibility of aggregation of the nanoparticles 11N in Z direction.

FIG. 3E is a top view of FIG. 3D. Dispersed nanoparticles 11N shown in FIG. 3E display the real dispersion status of nanoparticles 11N in the original blood sample 11 as shown in FIG. 3B.

FIGS. 4A-E illustrate the second specimen prepared according to the present invention.

FIG. 4A shows a blood sample 11 ready to be injected into a chamber 20 of a specimen kit. The blood sample 11 contains nanoparticle-agglomerates 11NA, nanoparticles 11N, and blood cells 11C. The chamber 20 is formed between a top substrate 20T and a bottom substrate 20B. The height h between the top substrate 20T and the bottom substrate 20B is less than the diameter of an RBC. Thus, all blood cells 11C are screened from entering the chamber 20.

FIG. 4B shows both nanoparticles 11N and nanoparticle-agglomerates 11NA in a blood sample 11 entering the chamber 20. Blood cells 11C do not enter the chamber 20 due to their larger dimensions.

FIG. 4C shows a drying process is performed to the blood sample 11 of FIG. 4B. The blood sample 11 within the chamber 20 is dried and a plurality of small droplets are formed. Each droplet wraps a single nanoparticle and attaches onto the inner surface of the chamber 20 due to the adhesion force 13 of the droplet.

FIG. 4D shows some nanoparticles 11N and nanoparticle-agglomerates 11NA attached to the bottom surface of the top substrate 20T, and some nanoparticles 11N and nanoparticle-agglomerates 11NA attached to the top surface of the bottom substrate 20B after drying. The tiny height h limits the numbers of nanoparticles 11N and nanoparticle-agglomerates 11NA distributed especially in Z direction, and hence eliminates the possibility of aggregation of nanoparticles 11N and nanoparticle-agglomeration 11NA in Z direction.

FIG. 4E shows the top view of FIG. 4D. The dispersed nanoparticles 11N and nanoparticle-agglomerates 11NA in the specimen display the real situation of nanoparticles 11N and nanoparticle-agglomerates 11NA distributed in the original blood sample 11 as shown in FIG. 4B.

Figure 5:
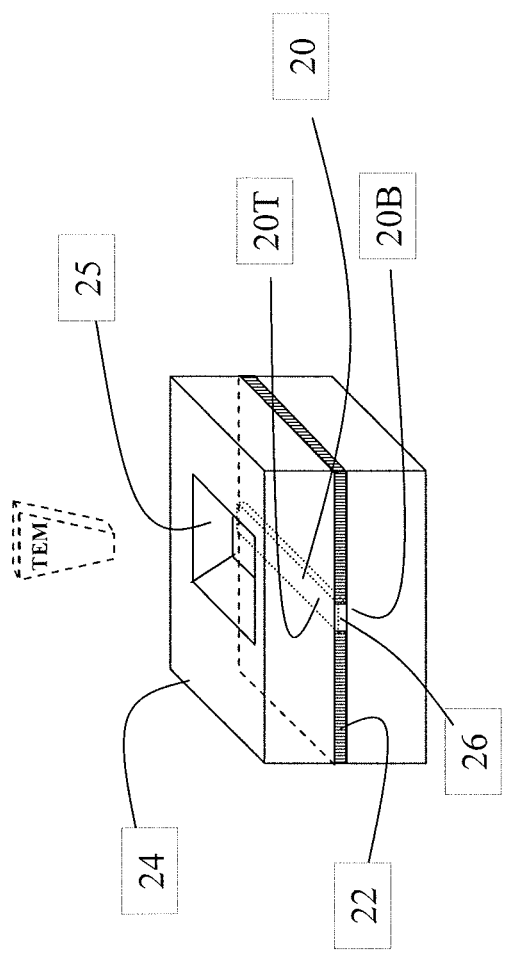
FIG. 5 is a perspective view of a specimen kit.

FIG. 5 is a perspective view of a specimen kit.

FIG. 5 shows a specimen kit suitable for preparing a specimen for observation under a TEM. The kit has a chamber 20 formed between a top substrate 20T and a bottom substrate 20B. The height h of the chamber 20 is smaller than the diameter of an RBC, and the top substrate 20T is made of a material transparent to electrons. A chamber height of 10 μm is enough for TEM observation of the distribution status of nanoparticles in a blood sample 11, either in dispersion or agglomeration. A spacer 22 is inserted between the substrates to control the height. A solution entrance 26 is configured for injection of a sample. Observation window 25 is made at the center and on the top of a frame 24 of the kit. Part of the chamber 20 is exposed to the window 25 for TEM observation from the top of the kit.

Figure 6:
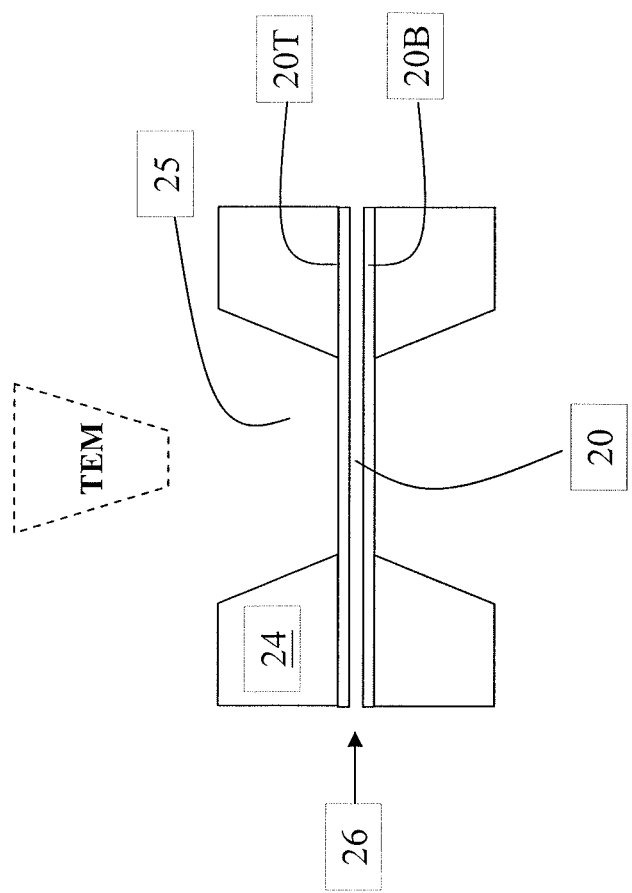
FIG. 6 is a section view of the first specimen kit according to the present invention.

FIG. 6 is a section view of the first specimen kit according to the present invention.

FIG. 6 shows a chamber 20 formed between a top substrate 20T and a bottom substrate 20B. An observation window 25 is made at the center and on the top of a frame 24 of the kit. Part of the chamber 20 is exposed to the window 25 for TEM observation from the top of the kit. A solution entrance 26 is configured for sample injection.

Figure 7A:
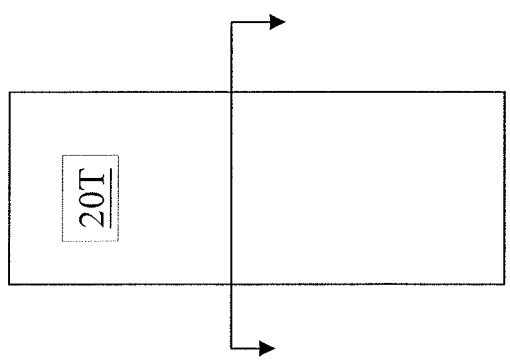
FIGS. 7A-B illustrate the top substrate 20T and the chamber of the first specimen kit, respectively.
Figure 7B:
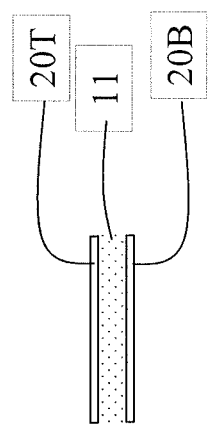

FIGS. 7A-B illustrate the top substrate 20T and the chamber of the first specimen kit.

FIG. 7A shows the top view of the chamber 20 of the first specimen kit. The top substrate 20T is a flat panel transparent to electrons. FIG. 7B is a section view of FIG. 7A, showing the top substrate 20T and the bottom substrate 20B, and a blood sample 11 filled in the chamber between the substrates 20T, 20B.

FIGS. 8A-B illustrate the top substrate 30T and the chamber of the second specimen kit.

FIG. 8A is a top view of the second specimen kit, showing the top substrate 30T and a plurality of through holes 31 made in the top substrate 30T. When a specimen with blood or liquid is present in the chamber, the holes 31 make observation of the specimen easier.

FIG. 8B is a section view of FIG. 8A, showing the top substrate 30T, the bottom substrate 30B, and a blood sample 11 filled in the chamber between the substrates 30T, 30B. Each hole is configured to be small enough to keep the blood sample 11 stay in the chamber due to a surface tension 33. Thus, the blood sample 11 does not seep through the holes 31.

FIGS. 9A-B show the top substrate 40T and the chamber of the second specimen kit.

FIG. 9A is a top view of the third specimen kit, showing the top substrate 40T, and a plurality of through grooves 41 made in the top substrate 40T. When a specimen with blood or liquid is present in the chamber, the grooves 41 made observation of the specimen easier.

FIG. 9B is a section view of FIG. 9A, showing the top substrate 40T, the bottom substrate 40B, and a blood sample 11 filled in the chamber between the substrates 40T, 40B. Each through groove 41 is configured to be small enough to keep the blood sample 11 stay in the chamber due to a surface tension 43. Thus, the blood sample 11 does not seep through the grooves 41.

While several embodiments have been described by way of examples, it will be apparent to those skilled in the an that various modifications may be configured without departing from the spirit of the present invention. Such modifications are all within the scope of the present invention, as defined by the appended claims.

What is claimed is:

1. A specimen kit for transmission electron microscopy (TEM), comprising:
   (a) a top substrate and a bottom substrate, wherein the top substrate is made of a material transparent to electrons;
   (b) a chamber formed between the substrates, wherein the height of the chamber is smaller than the diameter of a blood cell; and
   (c) a through hole or a through groove, made in the top substrate, wherein the through hole or the through groove is small enough to keep a blood sample in the chamber by a surface tension before drying the blood sample.

2. A method for preparing a specimen for TEM, comprising:

(i) preparing a blood sample containing nanoparticles;
(ii) providing the specimen kit of claim 1;
(iii) filling the chamber with the blood sample containing the nanoparticles; and
(iv) drying the blood sample containing the nanoparticles and leaving the nanoparticles precipitated.

3. A specimen kit for transmission electron microscopy (TEM), comprising:
(a) a top substrate and a bottom substrate, wherein the top substrate is made of a material transparent to electrons;
(b) a chamber formed between the substrates, wherein the height of the chamber is smaller than the diameter of a blood cell; and
(c) a blood sample filled into the chamber, wherein the blood sample contains nanoparticles.

4. The specimen kit of claim 3, wherein the height of the chamber is smaller than 10 μm.

5. A method for preparing a specimen for TEM, comprising:
(i) providing the specimen kit of claim 4; and
(ii) drying the blood sample containing the nanoparticles and leaving the nanoparticles precipitated.

6. A method for preparing a specimen for TEM, comprising:
(i) providing the specimen kit of claim 3; and
(ii) drying the blood sample containing the nanoparticles and leaving the nanoparticles precipitated.

7. The specimen kit of claim 3, further comprising:
a through hole or a through groove, made in the top substrate, wherein the through hole or the through groove is small enough to keep the blood sample in the chamber by a surface tension before drying the blood sample.

8. A method for preparing a specimen for TEM, comprising:
(i) providing the specimen kit of claim 7, and
(ii) drying the blood sample containing the nanoparticles and leaving the nanoparticles precipitated.

* * * * *